(12) United States Patent
Glasgow et al.

(10) Patent No.: US 7,078,447 B2
(45) Date of Patent: Jul. 18, 2006

(54) IONIZING RADIATION STABLE POLYARYLESTERCARBONATE COMPOSITIONS

(75) Inventors: Katherine Glasgow, Evansville, IN (US); Adam Zerda, Evansville, IN (US)

(73) Assignee: General Electric Company, Schenectady, NY (US)

( * ) Notice: Subject to any disclaimer, the term of this patent is extended or adjusted under 35 U.S.C. 154(b) by 122 days.

(21) Appl. No.: 10/718,979

(22) Filed: Nov. 21, 2003

(65) Prior Publication Data

US 2005/0113535 A1  May 26, 2005

(51) Int. Cl.
C08J 3/28 (2006.01)
C08K 5/053 (2006.01)
C08L 69/00 (2006.01)

(52) U.S. Cl. .................. 523/136; 524/112; 524/377; 524/386; 524/392; 525/408

(58) Field of Classification Search ................ 523/136; 524/377, 386; 525/408, 439
See application file for complete search history.

(56) References Cited

U.S. PATENT DOCUMENTS

| | | |
|---|---|---|
| 3,635,895 A | 1/1972 | Kramer |
| 4,001,184 A | 1/1977 | Scott |
| 4,217,438 A | 8/1980 | Brunelle et al. |
| 4,624,972 A | 11/1986 | Nace |
| 4,645,736 A | 2/1987 | Antonsen et al. |
| 4,657,949 A | 4/1987 | Nace |
| 4,686,245 A | 8/1987 | Nelson |
| 4,757,104 A | 7/1988 | Nace |
| 4,778,656 A | 10/1988 | Allen et al. |
| 4,804,692 A | 2/1989 | Lundy et al. |
| 4,873,271 A | 10/1989 | Lundy et al. |
| 4,874,802 A | 10/1989 | Lundy et al. |
| 4,880,850 A | 11/1989 | Nelson et al. |
| 4,880,855 A | 11/1989 | Nelson et al. |
| 4,880,856 A | 11/1989 | Avakian |
| 4,904,710 A | 2/1990 | Nace |
| 4,939,185 A | 7/1990 | Nelson et al. |
| 4,963,598 A | 10/1990 | Krishnan et al. |
| 4,996,248 A | 2/1991 | Nelson et al. |
| 5,006,572 A | 4/1991 | Lundy et al. |
| 5,118,726 A | 6/1992 | Mizutani et al. |
| 5,137,688 A | 8/1992 | DeRudder |
| 5,187,208 A | 2/1993 | Rodenhouse |
| 5,187,211 A | 2/1993 | Lundy et al. |
| 5,196,245 A | 3/1993 | DeRudder et al. |
| 5,214,078 A | 5/1993 | Powell et al. |
| 5,274,009 A | 12/1993 | Grigo et al. |
| 5,280,050 A | 1/1994 | Powell et al. |
| 5,382,605 A | 1/1995 | Powell et al. |
| 5,399,658 A | 3/1995 | Archey et al. |
| 5,453,457 A | 9/1995 | Meltzer et al. |
| 5,464,893 A | 11/1995 | Archey et al. |
| 5,476,893 A | 12/1995 | Lundy et al. |
| 5,491,179 A | 2/1996 | Mason |
| 5,599,863 A | 2/1997 | Zimmerman |
| 5,608,027 A | 3/1997 | Crosby et al. |
| 5,612,398 A | 3/1997 | Fennhoff et al. |
| 5,672,664 A | 9/1997 | DeRudder et al. |
| 5,681,905 A | 10/1997 | Mason et al. |
| 5,684,062 A | 11/1997 | Ebert et al. |
| 5,744,517 A | 4/1998 | Chung |
| 5,773,491 A | 6/1998 | Ebert et al. |
| 5,807,908 A | 9/1998 | Hirose et al. |
| 5,852,070 A | 12/1998 | Ebert et al. |
| 5,936,007 A | 8/1999 | Ebert et al. |
| 5,948,838 A | 9/1999 | Miya et al. |
| 6,008,280 A | 12/1999 | Krishnan et al. |
| 6,040,367 A | 3/2000 | Miya et al. |
| 6,166,116 A | 12/2000 | Sleeckx |
| 6,197,853 B1 | 3/2001 | Bolton et al. |
| 6,197,854 B1 | 3/2001 | Krishnan et al. |
| 6,559,270 B1 | 5/2003 | Siclovan et al. |
| 6,897,245 B1 | 5/2005 | Gen |

FOREIGN PATENT DOCUMENTS

| | | |
|---|---|---|
| EP | 0 152 012 A2 | 8/1985 |
| EP | 0 439 763 A2 | 8/1991 |
| EP | 0 228 525 B1 | 1/1992 |
| EP | 0 315865 B1 | 1/1992 |
| EP | 0 296 473 B1 | 10/1992 |
| EP | 0 572 889 A1 | 12/1993 |
| EP | 0 359 366 B1 | 3/1994 |
| EP | 0 338 319 B1 | 6/1995 |
| EP | 0 664 316 A1 | 7/1995 |
| EP | 0 346 706 B1 | 11/1995 |
| EP | 0 376 289 B1 | 11/1995 |
| EP | 0 687 710 A2 | 11/1995 |
| EP | 0 384 110 B1 | 12/1995 |
| EP | 0 598 043 B1 | 2/1996 |
| EP | 0 611 797 B1 | 12/1998 |
| EP | 01 004 621 A1 | 5/2000 |
| WO | WO 00/75223 A1 | 2/2000 |
| WO | WO-00/26275 * | 5/2000 |
| WO | WO 01/02474 A1 | 1/2001 |
| WO | WO 02/15725 A2 | 2/2002 |

* cited by examiner

Primary Examiner—David J. Buttner

(57) ABSTRACT

Embodiments of ionizing radiation stable polyarylestercarbonate resin compositions, methods for making the ionizing radiation stable compositions, and articles and medical devices made from these ionizing radiation stable compositions are disclosed. For examples the specification discloses a composition which comprises a block copolyarylestercarbonate and a ionizing radiation stablizing additive. The said copolyarylestercarbonate comprises an organic carbonate block and at least one arylate block. The arylate block comprises arylate structural units derived from at least one 1,3-dihydroxybenzene moiety and at least one aromatic dicarboxylic acid moiety. The arylate block has a degree of polymerization of 1 or greater.

18 Claims, 8 Drawing Sheets

Effect of Polyester Content on dYI After Ionizing Radiation Sterilization

5% polyester with increasing hexylene glycol concentration

Figure 6

Effect of Polyester Content on dYI after Ionizing Radiation Sterilization

| | Yellowness shift (dYI) | | |
|---|---|---|---|
| % polyester | 25 kGy | 50 kGy | 75 kGY |
| 0 | 23.4 | 39.0 | 60.6 |
| 5 | 17.1 | 26.6 | 37.1 |
| 13 | 13.4 | 20.2 | 30.0 |
| 20 | 10.5 | 16.8 | 25.8 |

Figure 7

Effect of % Hexylene Glycol on dYI After Ionizing Radiation Sterilization

Yellowness Shift (dYI)

*0% polyester*

| % HG | 25 kGy | 50 kGy | 75 kGy |
|---|---|---|---|
| 0.00 | 25.5 | 41.0 | 62.6 |
| 0.05 | 19.5 | 33.0 | 54.1 |
| 0.08 | 17.4 | 31.8 | 54.2 |
| 0.10 | 16.3 | 29.4 | 52.7 |
| 0.13 | 14.3 | 27.3 | 50.1 |
| 0.20 | 13.0 | 23.4 | 43.7 |

*5% polyester*

| % HG | 25 kGy | 50 kGy | 75 kGy |
|---|---|---|---|
| 0.0 | 19.4 | 28.9 | 39.4 |
| 0.1 | 9.1 | 14.2 | 24.6 |

Figure 8
dYI Changes After Photobleaching for Stabilized & UnstabilizedResins

| Batch | [Hexylene glycol] (%) | [Polyester] (%) | 25 kGy | | | | | 50 kGy | | | | | 75 kGy | | | |
|---|---|---|---|---|---|---|---|---|---|---|---|---|---|---|---|---|
| | | | 0 days | 7 days | 14 days | 21 days | 28 days | 0 days | 7 days | 14 days | 21 days | 28 days | 0 days | 7 days | 14 days | 21 days |
| 1 | 0.2 | 5 | 5.99 | 3.09 | 2.58 | 2.21 | 2.01 | 9.56 | 5.13 | 4.32 | 3.78 | 3.55 | 18.39 | 9.32 | 7.71 | 6.57 |
| 2 | 0.1 | 13 | 6.34 | 3.35 | 2.90 | 2.54 | 2.33 | 11.04 | 5.78 | 4.95 | 4.69 | 4.25 | 18.51 | 9.17 | 7.91 | |
| 3 | 0.1 | 5 | 6.95 | 3.58 | 2.97 | 2.64 | 2.48 | 12.02 | 6.25 | 5.20 | 4.32 | 3.95 | 22.42 | 9.49 | 8.54 | 7.42 |
| 4 | 0.2 | 5 | 5.53 | 2.94 | 2.51 | 2.06 | 1.91 | 9.09 | 4.79 | 4.03 | 3.51 | 3.15 | 17.31 | 7.86 | 6.92 | 6.06 |
| 5 | 0.0 | 20 | 10.55 | 5.23 | 4.36 | 3.75 | 3.46 | 16.77 | 8.85 | 7.04 | 6.33 | 6.01 | 25.79 | 13.17 | 10.99 | 9.35 |
| 6 | 0.1 | 5 | 6.77 | 3.60 | 2.85 | 2.41 | 2.27 | 11.48 | 5.86 | 4.94 | 4.26 | 3.87 | 21.74 | 9.42 | 8.24 | 7.09 |
| 7 | 0.0 | 13 | 13.63 | 6.40 | 5.00 | 4.37 | 4.07 | 20.24 | 10.74 | 8.25 | 7.03 | 6.71 | 29.98 | 17.95 | 13.22 | 10.42 |
| 8 | 0.0 | 13 | 13.37 | 6.48 | 5.17 | 4.70 | 4.21 | 19.99 | 9.22 | 7.44 | 6.80 | 6.16 | 28.64 | 17.04 | 12.67 | 10.62 |
| 9 | 0.0 | 5 | 17.11 | 7.87 | 5.76 | 5.13 | 4.44 | 26.59 | 12.59 | 8.71 | 7.13 | 6.67 | 37.13 | 19.29 | 13.68 | 11.53 |
| 10 | 0.1 | 13 | 6.40 | 3.48 | 2.97 | 2.60 | 2.44 | 10.65 | 5.49 | 4.83 | 4.30 | 3.85 | 18.26 | 9.93 | 7.91 | 7.33 |
| 11 | 0.2 | 20 | 6.42 | 3.44 | 2.91 | 2.73 | 2.38 | 10.45 | 5.92 | 5.18 | 4.35 | 4.08 | 17.43 | 9.90 | 8.35 | 7.36 |
| 12 | 0.0 | 5 | 15.23 | 6.66 | 5.32 | 4.64 | 4.08 | 24.65 | 11.74 | 8.21 | 7.07 | 6.05 | 38.11 | 23.56 | 17.07 | 12.30 |
| 13 | 0.2 | 5 | 5.93 | 3.11 | 2.61 | 2.41 | 2.16 | 9.46 | 4.72 | 4.09 | 3.65 | 2.56 | 17.13 | 8.89 | 7.35 | 6.53 |
| 14 | 0.2 | 5 | 5.93 | 3.11 | 2.63 | 2.25 | 2.01 | 9.68 | 5.19 | 4.47 | 3.87 | 3.55 | 18.38 | 9.30 | 7.65 | 6.38 |
| 15 | 0.1 | 5 | 6.59 | 3.49 | 2.91 | 2.59 | 2.39 | 11.61 | 5.49 | 4.80 | 4.16 | 3.86 | 21.01 | 10.75 | 8.70 | 7.45 |
| 16 | 0.0 | 5 | 16.30 | 7.29 | 5.53 | 4.74 | 4.29 | 25.11 | 12.40 | 8.45 | 7.06 | 6.50 | 37.29 | 18.84 | 13.66 | 10.83 |
| 17 | 0.0 | 0 | 24.26 | 9.33 | 6.34 | 5.08 | 4.59 | 40.57 | 22.61 | 14.22 | 10.67 | 8.67 | 59.99 | 32.09 | 23.43 | 16.90 |
| 18 | 0.1 | 0 | 14.08 | 5.69 | 4.68 | 3.68 | 3.12 | 26.57 | 11.76 | 8.53 | 6.81 | 6.12 | 47.95 | 24.29 | 16.47 | 12.63 |
| 19 | 0.2 | 0 | 11.28 | 4.96 | 4.07 | 3.32 | 2.85 | 21.68 | 10.19 | 7.63 | 5.92 | 5.56 | 41.92 | 16.12 | 12.99 | 11.03 |

IONIZING RADIATION STABLE POLYARYLESTERCARBONATE COMPOSITIONS

BACKGROUND OF INVENTION

This disclosure relates to an ionizing radiation stable polyarylestercarbonate composition, and especially relates to an ionizing radiation stable polyarylestercarbonate composition suitable for use in medical devices which are sterilized using ionizing radiation sterilization. It also relates to methods for making the ionizing radiation stable composition and the articles suitable for use in medical applications produced from these ionizing radiation stable compositions.

A common procedure for plastics used in medical devices is to subject them to sterilization in order to reduce the possibility of infection to patients undergoing medical procedures. Sterilization can be carried out during the time after the molding of the part and prior to shipment to the medical institution by the company supplying the medical article or a third party contracted by the molder or at the medical institution prior to use in a medical procedure. Four common methods of sterilization are used for sterilizing plastic articles: ionization sterilization using ionizing radiation such as gamma or E-beam irradiation at dosages of 25–50 kGy, autoclaving using saturated steam at 121° C. to 130° C., dry heat sterilization and ethylene oxide gas sterilization. Other sterilization practice involves the use of multiple sterilization steps, where the above described common methods of sterilization are repeated or used in combination.

Polycarbonate is a particularly suitable thermoplastic employed in devices used by the medical industry because of its high reliability and safety benefits resulting from its optical transparency, toughness and heat resistance. Common medical devices made from polycarbonate include syringes, blood filter housings, intravenous connectors and parts for use in dialysis equipment among many others.

Polycarbonate articles are well known by those skilled in the art to perform well and resist discoloration after ethylene oxide gas sterilization and autoclaving sterilization. But when high energy irradiation sterilization methods are used, polycarbonate has a tendency to become discolored even though its mechanical properties have not generally been compromised (FIG. 1). Discoloration is undesirable for medical applications because it impacts the transparency of the article. The loss of transparency due in part to severe yellowing can severely damage the function and safety of the medical devices because monitoring of blood or other liquid flow may be severely hindered. Severe discoloration is also undesirable because medical devices with a compromised appearance can undermine the confidence of a patient undergoing treatment using such a polycarbonate medical device.

The discoloration of polycarbonate when treated with high-energy radiation such as gamma or E-beam radiation is thought to result from production of highly energetic and unstable species along the polycarbonate backbone. These species result in a yellow appearance and some loss of optical clarity of the polycarbonate article. The degree of yellowness and loss of optical clarity depends on the irradiation dosage.

The initial yellowness produced upon irradiation normally decreases with time and with further normal light exposure (FIG. 2). This color reversal is known by those skilled in the art as photobleaching. Eventually, the photobleached part reaches a steady state color shift, which is more yellow and less transparent than the part prior to initial irradiation, but less yellow and more transparent than immediately following initial irradiation. The length of time required to reach the steady state yellow color depends on the radiation dosage and the amount of normal room light exposure the part receives after the irradiation process.

A variety of additives have been developed to reduce the color shift in polycarbonate resulting from E-beam or gamma irradiation, including, but not limited to, bromine-containing additives, sulfide-containing additives, and polymeric and non-polymeric alcohols such as glycols. Also, blends of polycarbonate with more ionizing radiation stable polymers such as certain polyesters have been tried for this purpose. These solutions are effective to varying degrees to reduce yellowness and loss of optical transparency, but they can also adversely impact the physical properties and transparency of the polycarbonate article.

Prior to the invention of the compositions and methods described herein, polycarbonate compositions for the medical industry were well known for their tendency to undergo severe yellowing and loss of transparency when subjected to the high energy levels associated with ionizing radiation sterilization. As noted, these changes are highly undesirable in the medical industry. Ionizing radiation sterilization methods are becoming the preferred sterilization method for medical suppliers to hospitals. Therefore, it has been apparent that the continued use of polycarbonate resin in medical device applications (e.g., bottles, instruments, etc.) will be severely limited unless a composition and/or method can be found to mitigate the tendency of polycarbonate to yellow and lose transparency upon ionizing radiation sterilization.

SUMMARY

It has been surprisingly discovered that the presence of resorcinol derived ester units in polyarylestercarbonate compositions and blends is particularly effective in improving the tendency of such resins to yellow and lose transparency after an ionizing radiation sterilization processes. This performance is further improved by addition of ionizing radiation stabilization additives to the resorcinol-containing polyarylestercarbonate formulations and blends.

Prior to Applicants' discovery it was assumed that the only possible way to improve the ionizing radiation stabilization performance of polycarbonate was through the use of expensive additives, which resulted in only marginal ionizing radiation resistance improvement, and often introduced other undesirable environmental and possibly toxicological qualities rendering them unsuitable for medical use, or alternatively, the use of expensive co-monomers which often compromised the highly desirable mechanical properties of polycarbonate such as toughness, heat resistance and hydrolytic stability performance. The solution presented herein substantially overcomes these problems.

Disclosed herein are ionizing radiation stable copolyarylester compositions, methods for making said compositions, articles made from said compositions, medical devices made from said compositions, ionizing radiation stable performance properties of medical devices made from said compositions, and methods for sterilizing medical devices.

In one embodiment of the invention, an ionizing radiation stable composition comprises a block copolyarylestercarbonate and a ionizing radiation stable additive. The block copolyarylester-carbonate comprises an organic carbonate block (typically multiple blocks), and at least one arylate block (again, typically multiple). The arylate block in turn comprises arylate structural units derived from a 1,3-dihydroxybenzene (resorcinol) moiety and at least one aromatic dicarboxylic acid moiety (which can be the acid or an acid halide derivative thereof). The arylate block has a degree of polymerization of 1 or greater.

In another embodiment, a method for making the ionizing radiation stable composition comprises the following steps. First, a block copolyarylestercarbonate having the above desired structure is prepared. Next, the block copolyarylestercarbonate is combined with an ionizing radiation stable additive to form the ionizing radiation stable composition.

In another embodiment of the inventions an article is molded from the ionizing radiation stable composition described above.

In another embodiment of the invention, a medical device is fabricated. At least part of the device is made from a composition comprising the polyarylester-carbonate described above. The composition may further comprise an ionizing radiation stable additive.

Another example of the invention is a medical device that comprises a block copolyarylestercarbonate having a yellowness shift of less than 10 yellowness index units after sterilization with 25 kGy of ionizing radiation. Typically, a medical device from the ionizing radiation stable composition described above will have such properties.

Yet another example of the invention is a process for sterilizing a medical device by applying ionizing radiation to a device comprising the aforementioned block copolyarylestercarbonate, an optionally also the ionizing radiation stable additive.

BRIEF DESCRIPTION OF DRAWINGS

Refering now to the following Figures in which:

FIG. 6 is a table providing data shown in FIG. 3.

FIG. 7 is a table providing the data shown in FIGS. 4 and 5.

FIG. 8 is a table showing the changes in yellowness (dYI) for samples which received ionizing radiation radiation dosages of 25 kGy or 75kGy and then allowed to age in the dark for 14 days and then exposed to light for 28 days with changes in yellowness (dYI) measurements recorded on a regular schedule.

DETAILED DESCRIPTION OF INVENTION

Figure 1:
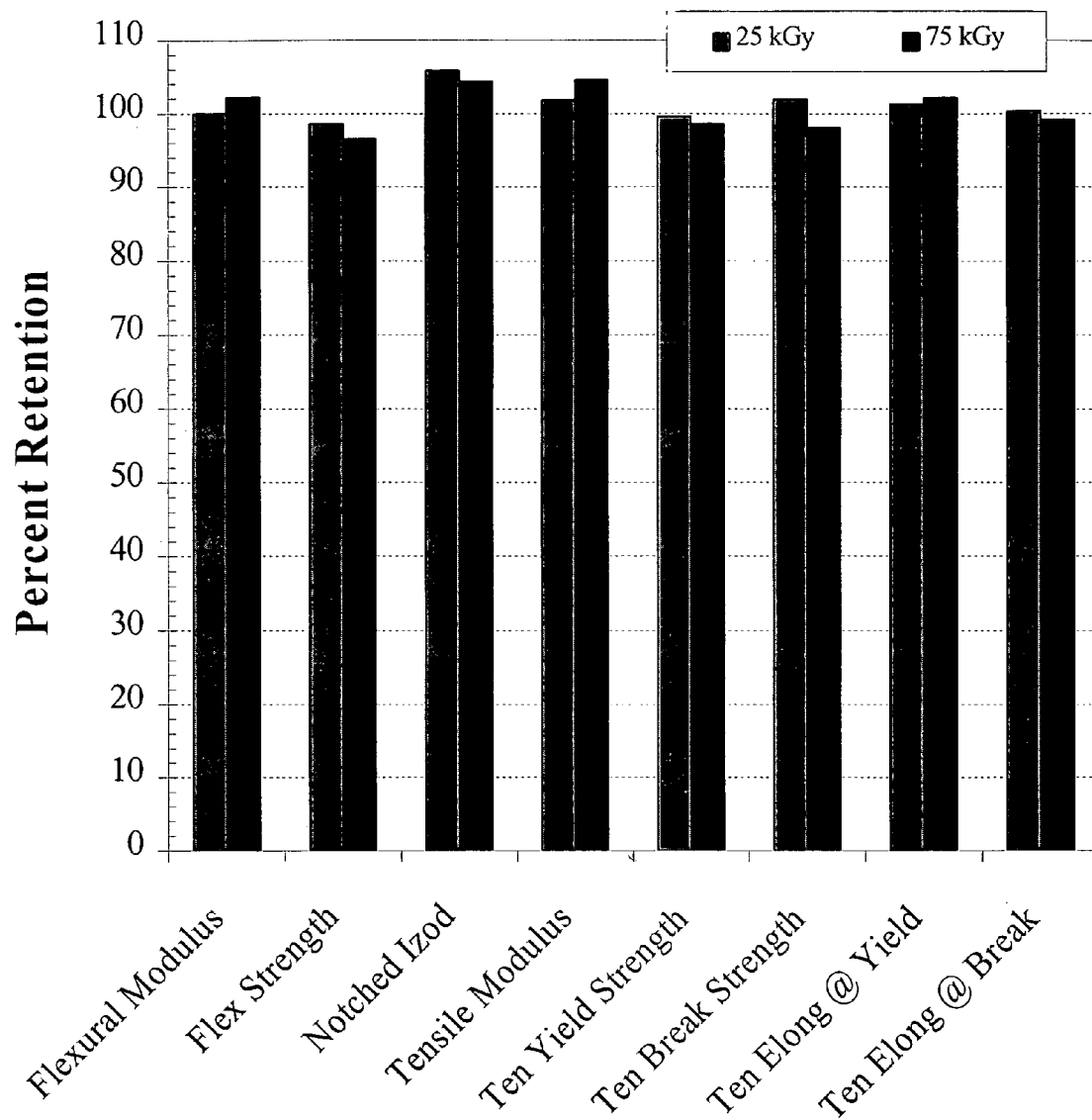
FIG. 1 is a graphical representation of mechanical property retention of polycarbonate articles made from polycarbonate (not polyarylestercarbonate) compositions which have a ionizing radiation stabilization additive, hexylene glycol, present at a level of about 0.1 wt. % based on the weight of polycarbonate after ionizing radiation irradiation at dosages of 25 kGy and 75 kGy.
Figure 2:
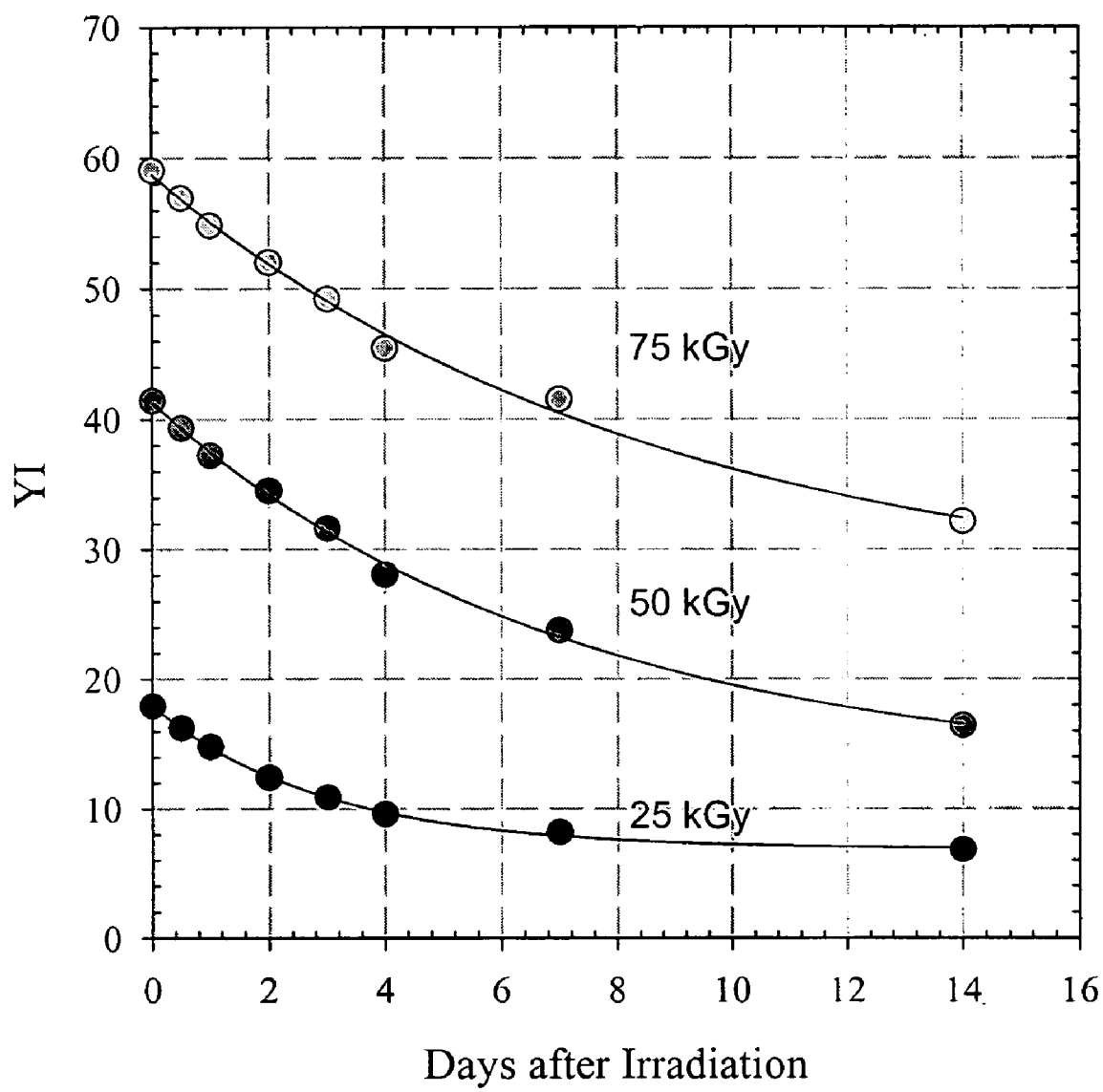
FIG. 2 is a graphical representation of the changes in the yellowness index (dYI) with time of polycarbonate articles (not polyarylestercarbonate) made from polycarbonate compositions, which have a ionizing radiation stabilization additive, hexylene glycol, present at a level of about 0.1 wt. %, based on the weight of polycarbonate, after ionizing radiation irradiation at dosages of 25 kGy, 50 kGy and 75 kGy.

As used herein, the term "ionizing radiation stable" composition refers to a thermoplastic resin formulation, which shows a low tendency to undergo yellowing on exposure to ionizing radiation. A change in yellowness is described herein as a "yellowness shift" (abbreviated as dYI). For a composition hat contains an ionizing radiation stabilizing additive to be considered ionizing radiation stable, the yellowness shift should be less than 30 dYI at a dosage level of 75 kGy. For a composition that does not contain a gamma stabilizing additive to be considered ionizing radiation stable, the yellowness shift should be less than 40 dYI at a dosage level of 75 kGy.

As used herein the term "ionizing radiation" refers to energy in the form of gamma or E-beam radiation. Typical dosage levels of ionizing radiation in the medical industry are in the range of 25 to 50 kGy. However it is common in the industry to test for stability to ionizing radiation at dosage levels of 75 kGy.

As used herein the term "sterilization" refers to procedures employed by those skilled in the art in the medical industry to destroy organisms on the thermoplastic medical articles capable of causing infection to patients who would be exposed to these during their medical treatment. Common forms of sterilization employed by the medical industry include steam sterilization, dry heat sterilization, ethylene oxide gas sterilization and ionizing radiation.

As used herein the term "ionizing radiation sterilization" refers to a sterilization process that involves exposure of articles or devices to ionizing radiation at a specific dosage level. Dosage levels are measured in units of kiloGrays (abbreviated as kGy herein). Another common unit of measure for ionizing radiation dosage levels is a megaRad (commonly abbreviated as MR). 10 kGy is equal to 1 MR. Typical dosages employed in medical article sterilization are 25 kGy and 50 kGy. However the yellowness testing of a potentially new ionizing radiation stable composition is commonly conducted at the more severe dosage level of 75 kGy.

As used herein the term "moiety" refers to a part of a polymeric structure corresponding to a particular starting material which may have lost atoms during the polymerization. For example, a 1,3 dihydroxybenzene moiety would correspond to resorcinol without the hydrogen atoms on its hydroxyl groups as liked into the polymer.

The words "polyarylestercarbonate" and "copolyarylestercarbonate" are used interchangeably herein and are intended to have the same meaning.

As used herein the term "photobleaching" means the tendency of resins to undergo a reversal of yellowness after the initial yellowness color change resulting from ionizing radiation radiation treatment. This reversal does occur even in the dark, but is accelerated when the resins are exposed to light. Eventually, as steady state is reached, a permanent color shift is observed, and no significant further photobleaching occurs.

As used herein the term "ionizing radiation stabile additive" refers to an additive typically mixed with a thermoplastic resin composition to reduce the tendency of the resultant thermoplastic resin composition to undergo yellowing after exposure to ionizing radiation. These additives vary in their effectiveness to reduce yellowing of thermoplastic resin compositions depending on the thermoplastic resin and the type of ionizing radiation stable additive present in thermoplastic resin composition. Common ionizing radiation stable additives employed with polycarbonate resin compositions include, but are not limited to, brominated additives such as tetrabromophthalic anhydride and blends with brominated polycarbonates, sulfide additives such as diphenylsulfide, aliphatic alcohols such as hexyleneglycol (2-methyl-2,4-pentanediol), and polyaliphatic alcohols such as hexylene glycol, polyethylene glycol and polypropylene glycol. It is also known that polymers can be blended with polycarbonate to reduce its tendency to yellow on exposure to ionizing radiation. Some non-limiting examples of such polymers include: poly(1,4-cyclohexanedimethanol)terephthalate, copolymers of 1,4-cyclohexanedimethanol, copolymers of ethylene glycol and terephthalic acid, and polyamides. Among these, glycols are preferred.

The block copolyarylestercarbonates of the present invention typically comprise alternating organic carbonate and arylate blocks. They include polymers comprising moieties of the formula (I) below.

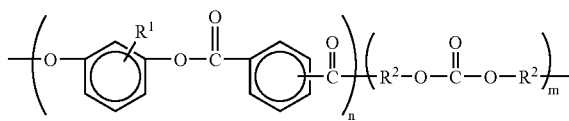

(I)

wherein $R^1$ is hydrogen, halogen or $C_{1-4}$ alkyl, each $R^2$ is independently a divalent organic radical, m is at least about 1 and n is at least about 1. The arylate blocks thus contain a 1,3-dihydroxybenzene moiety which may be substituted with halogen, usually chorine or bromine, or with $C_{1-4}$ alkyl; i.e., methyl, ethyl, propyl or butyl. Said alkyl groups are preferably primary or secondary groups, with methyl being more preferred, and are most often located in the ortho position to both oxygen atoms although other locations are also possible. The most preferred moieties are resorcinol moieties, in which $R^1$ is hydrogen. In one embodiment, $R^1$ is hydrogen, the $R^2$ groups are each independently resorcinol or Bisphenol-A moieties, and the copolyarylestercarbonate end groups can be hydroxyl groups, carboxylic acid groups, phenyl groups or mixtures thereof.

Said 1,3-dihydroxybenzene moieties are bound to aromatic dicarboxylic acid moieties which may be monocyclic moieties, e.g., isophthalate or terephthalate, or polycyclic moieties, e.g., naphthalenedicarboxylate. Preferably, the aromatic dicarboxylic acid moieties are isophthalate and/or terephthalate. Either or both of said moieties may be present. For the most part, both are present in a molar ratio of isophthalate to terephthalate in the range of about 0.25–4.0: 1, preferably about 0.8–2.5:1.

In the carbonate blocks, each $R^2$ is independently an organic radical. For the most part, at least about 60 percent of the total number of $R^2$ groups in the polymer are aromatic organic radicals and the balance thereof are aliphatic, alicyclic, or aromatic radicals. Suitable $R^2$ radicals include m-phenylene, p-phenylene, 4,4'-biphenylene, 4,4'-bi(3,5-dimethyl)-phenylene, 2,2-bis(4-phenylene)propane and similar radicals such as those which correspond to the dihydroxy-substituted aromatic hydrocarbons disclosed by name or formula (generic or specific) in U.S. Pat. No. 4,217,438, which is incorporated herein by reference.

More preferably, each $R^2$ is an aromatic organic radical and still more preferably a radical of the formula $$-A^1-Y-A^2-,$$  (II)

wherein each $A^1$ and $A^2$ is a monocyclic divalent aryl radical and Y is a bridging radical in which one or two carbon atoms separate $A^1$ and $A^2$. The free valence bonds in formula II are usually in the meta or para positions of $A^1$ and $A^2$ in relation to Y. Compounds in which $R^2$ has formula II are bisphenols, and for the sake of brevity the term "bisphenol" is sometimes used herein to designate the dihydroxy-substituted aromatic hydrocarbons; it should be understood, however, that non-bisphenol compounds of this type may also be employed as appropriate.

In formula II, $A^1$ and $A^2$ typically represent unsubstituted phenylene or substituted derivatives thereof, illustrative substituents (one or more) being alkyl, alkenyl, and halogen (particularly bromine). Unsubstituted phenylene radicals are preferred. Both $A^1$ and $A^2$ are preferably p-phenylene, although both may be o- or m-phenylene or one o- or m-phenylene and the other p-phenylene.

The bridging radical, Y, is one in which one or two atoms separate $A^1$ from $A^2$. The preferred embodiment is one in which one atom separates $A^1$ from $A^2$. Illustrative radicals of this type are —O—, —S—, —SO— or —SO2—, methylene, cyclohexyl-methylene, 2-[2.2.1]-bicycloheptyl methylene, ethylene, isopropylidene, neopentylidene, cyclohexylidene, cyclopentadecylidene, cyclododecylidene, adamantylidene, and the 2,2,2',2'-tetrahydro-3,3,3',3'-tetramethyl-1,1'spirobi[1H-indene]6,6'-diols having the following formula (III);

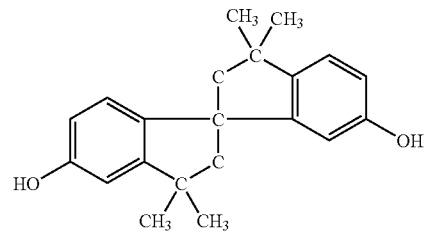

(III)

Gem-alkylene (alkylidene) radicals are preferred. Also included, however, are unsaturated radicals. For reasons of availability and particular suitability for the purposes of this invention, the preferred bisphenol is 2,2-bis(4-hydroxyphenyl)propane ("BPA" or bisphenol-A), in which Y is isopropylidene and $A^1$ and $A^2$ are each p-phenylene.

The arylate blocks have a degree of polymerization (DP), represented by n, of at least about 1, preferably about 10 to 50. The DP of the carbonate blocks, represented by m, is generally at least about 1, and preferably about 10 to 50.

The distribution of the blocks may be such as to provide a copolymer having any desired weight proportion of arylate blocks in relation to carbonate blocks. In general, copolymers containing about 1–99% by weight arylate blocks are preferred. Typically the arylate blocks are present at about 3–85% by weight.

In the first step A of a method of this invention for the preparation of block copolyestercarbonates, a 1,3-dihydroxybenzene which may be resorcinol (preferably) or an alkyl- or haloresorcinol may be contacted under aqueous alkaline reactive conditions with at least one aromatic dicarboxylic acid chloride, preferably isophthaloyl chloride, terephthaloyl chloride or a mixture thereof. The alkaline conditions are typically provided by introduction of an alkali metal hydroxide, usually sodium hydroxide. A catalyst, most often a tertiary amine such as triethylamine, or quaternary salts such as tetraalkylammonium, tetraalkylphosphonium or hexaalkylguanidinium halide, are usually also present, as is an organic solvent, generally a water-immiscible solvent and preferably a chlorinated aliphatic compound such as methylene chloride. Thus, the reaction is generally conducted in a 2-phase system.

In order to afford a hydroxy-terminated polyester intermediate, the molar ratio of resorcinol to acyl chlorides is preferably greater than 1:1. Base may be present in a molar ratio to acyl halides of about 2–2.5:1. Catalyst is usually employed in the amount of about 0.1–10 mole percent based on combined acyl halides. Reaction temperatures are most often in the range of about 25–50° C.

Following the completion of polyester intermediate preparation, it is sometimes advantageous to acidify the aqueous phase of the two-phase system with a weak acid prior to phase separation. The organic phase, which contains the polyester intermediate, is then subjected to a second step B which is the block copolyestercarbonate-forming reaction. It is also contemplated, however, to proceed to step B without acidification or separation, and this is often possible without loss of yield or purity.

It is also within the scope of the invention to prepare the polyester intermediate entirely in an organic liquid, with the use of a base soluble in said liquid. Suitable bases for such use include tertiary amines such as triethylamine.

The dihydroxyaromatic compound employed in the second step typically has the formula HO—$R^2$—OH, wherein $R^2$ is as previously defined. Bisphenol A is generally preferred. The carbonyl halide is preferably phosgene. This reaction may be conducted according to art-recognized interfacial procedures (i.e., also in a 2-phase system), employing a suitable interfacial polymerization catalyst and an alkaline reagent, again preferably sodium hydroxide, and optionally a branching agent such as 1,1,1-tris(4-hydroxyphenyl)ethane and/or a chain termination agent such as phenol or p-cumylphenol. To suppress scrambling of the block copolymer, the pH is maintained at a relatively low level, typically in the range of about 5–9, for the initial part of the phosgenation reaction; it may be increased to about 10–13 during the latter part of said reaction.

Following completion of both reactions, the block copolyarylestercarbonate may be isolated by conventional procedures. These may include, for example, anti-solvent precipitation, drying and pelletization via extrusion. It is also contemplated to conduct the first step by other ester-forming methods, as illustrated by transesterification using aromatic diesters and a 1,3-dihydroxybenzene either in a solvent or in the melt.

The block copolyarylestercarbonates of this invention are polymers having excellent physical properties. Their light transmitting properties are similar to those of polycarbonates. Thus, they are substantially transparent and may be employed as substitutes for polycarbonates in the fabrication of transparent sheet material when improved weatherability is mandated.

It is believed that the weatherability and other beneficial properties of the block copolyestercarbonates of the invention is attributable, at least in part, to the occurrence of a thermally or photochemically induced Fries rearrangement of the arylate blocks therein, to yield benzophenone moieties which serve as light stabilizers. For example, the moieties of formula (I) can rearrange to yield moieties of the formula (IV):

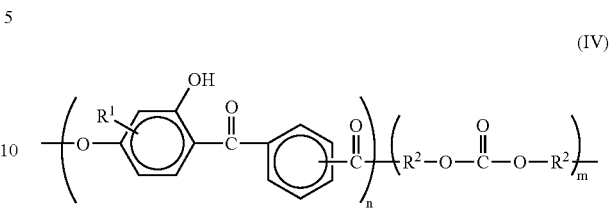

(IV)

wherein $R^1$, $R^2$, m and n are as previously defined. It is also contemplated to introduce moieties of formula (IV) via synthesis and polymerization.

One of the embodiments of the current invention involves blending of the polyarylestercarbonate compositions described above with one or more polycarbonates. As used herein, the terms "polycarbonate", "polycarbonate composition", and "composition comprising aromatic carbonate chain units" includes compositions having structural units of the formula (V):

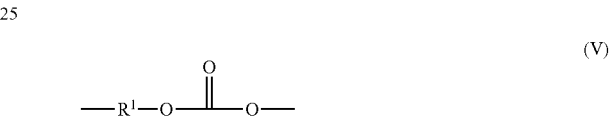

(V)

in which at least about 60 percent of the total number of $R^1$ groups are aromatic organic radicals and the balance thereof are aliphatic, alicyclic, or aromatic radicals. Preferably, $R^1$ is an aromatic organic radical and, more preferably, a radical of the formula (VI):

-$A^1$-$Y^1$-$A^2$-  (VI)

wherein each of $Z^1$ and $Z^2$ is a monocyclic divalent aryl radical and $B^1$ is a bridging radical having one or two atoms which separate $Z^1$ from $Z^2$. In an exemplary embodiment, one atom separates $Z^1$ from $Z^2$. Illustrative, non-limiting examples of radicals of this type are —O—, —S—, —S(O)—, —S(O$_2$)—, —C(O)—, methylene, cyclohexylmethylene, 2-[2,2,1]-bicycloheptylidene, ethylidene, isopropylidene, neopentylidene, cyclohexylidene, cyclopentadecylidene, cyclododecylidene, and adamantylidene. The bridging radical $B^1$ can be a hydrocarbon group or a saturated hydrocarbon group such as methylene, cyclohexylidene or isopropylidene.

Polycarbonates can be produced by the interfacial reaction of dihydroxy compounds in which only one atom separates $Z^1$ and $Z^2$. As used herein, the term "dihydroxy compound" includes, for example, bisphenol compounds having general formula (VII) as follows:

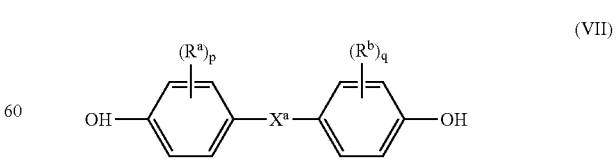

(VII)

wherein $R^a$ and $R^b$ each represent a halogen atom or a monovalent hydrocarbon group and may be the same or different; p and q are each independently integers from 0 to 4; and $X^a$ represents one of the groups of formula (VIII):

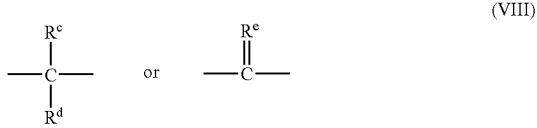

wherein $R^c$ and $R^d$ each independently represent a hydrogen atom or a monovalent linear or cyclic hydrocarbon group and $R^e$ is a divalent hydrocarbon group.

Some illustrative, non-limiting examples of suitable dihydroxy compounds include dihydric phenols and the dihydroxy-substituted aromatic hydrocarbons disclosed by name or formula (generic or specific) in U.S. Pat. No. 4,217,438. A nonexclusive list of specific examples of the types of bisphenol compounds that may be represented by formula (VII) includes the following: 1,1-bis(4-hydroxyphenyl) methane; 1,1-bis(4-hydroxyphenyl)ethane; 2,2-bis(4-hydroxyphenyl)propane (hereinafter "bisphenol A" or "BPA"); 2,2-bis(4-hydroxyphenyl)butane; 2,2-bis(4-hydroxyphenyl) octane; 1,1-bis(4-hydroxyphenyl)propane; 1,1-bis(4-hydroxyphenyl)n-butane; bis(4-hydroxyphenyl)phenylmethane; 2,2-bis(4-hydroxy-1-methylphenyl)propane; 1,1-bis(4-hydroxy-t-butylphenyl)propane; bis(hydroxyaryl) alkanes such as 2,2-bis(4-hydroxy-3-bromophenyl)propane; 1,1-bis(4-hydroxyphenyl)cyclopentane; and bis(hydroxyaryl)cycloalkanes such as 1,1-bis(4-hydroxyphenyl) cyclohexane; and the like, as well as combinations comprising at least one of the foregoing compounds.

It is also possible to employ polycarbonates resulting from the polymerization of two or more different dihydric phenols or a copolymer of a dihydric phenol with a glycol or with a hydroxy- or acid-terminated polyester or with a dibasic acid or with a hydroxy acid or with an aliphatic diacid in the event a carbonate copolymer rather than a homopolymer is desired for use. Generally, useful aliphatic diacids have from 2 to about 40 carbons. A preferred aliphatic diacid is dodecandioic acid. Polyarylates and polyester-carbonate resins or their blends can also be employed. Branched polycarbonates are also useful, as well as blends of linear polycarbonate and a branched polycarbonate. The branched polycarbonates may be prepared by adding a branching agent during polymerization.

These branching agents may comprise polyfunctional organic compounds containing at least three functional groups that may be hydroxyl, carboxyl, carboxylic anhydride, haloformyl, and mixtures comprising at least one of the foregoing groups. Specific examples include trimellitic acid, trimellitic anhydride, trimellitic trichloride, tris-p-hydroxy phenyl ethane, isatin-bis-phenol, tris-phenol TC (1,3,5-tris((p-hydroxyphenyl)isopropyl)benzene), tris-phenol PA (4(4(1,1-bis(p-hydroxyphenyl)-ethyl) alpha,alpha-dimethylbenzyl)phenol), 4-chloroformyl phthalic anhydride, trimesic acid and benzophenone tetracarboxylic acid, and the like. The branching agents may be added at a level of about 0.05 to about 2.0 weight percent, based upon the total weight of the resin. Branching agents and procedures for making branched polycarbonates are described in U.S. Pat. Nos. 3,635,895 and 4,001,184. All types of polycarbonate end groups are herein contemplated.

Preferred polycarbonates are based on bisphenol A, in which each of $Z^1$ and $Z^2$ is p-phenylene and $B^1$ is isopropylidene. Preferably, the weight average molecular weight of the polycarbonate is about 5,000 to about 100,000, more preferably about 10,000 to about 65,000, and most preferably about 15,000 to about 35,000.

The polyarylestercarbonate composition or blend may also include various additives ordinarily incorporated in resin compositions of this type. Such additives are, for example, fillers or reinforcing agents; heat stabilizers; antioxidants; light stabilizers; plasticizers; antistatic agents; mold releasing agents; additional resins; blowing agents; and the like, as well as combinations comprising at least one of the foregoing additives. Examples of fillers or reinforcing agents include glass fibers, asbestos, carbon fibers, silica, talc and calcium carbonate. Examples of heat stabilizers include triphenyl phosphite, tris-(2,6-dimethylphenyl)phosphite, tris-(mixed mono-and di-nonylphenyl)phosphite, dimethylbenzene phosphonate, and trimethyl phosphate. Examples of antioxidants include octadecyl-3-(3,5-di-tert-butyl-4-hydroxyphenyl)propionate, and pentaerythrityl-tetrakis[3-(3,5-di-tert-butyl-4-hydroxyphenyl)propionate].

Examples of light stabilizers include 2-(2-hydroxy-5-methylphenyl)benzotriazole, 2-(2-hydroxy-5-tert-octylphenyl)-benzotriazole and 2-hydroxy-4-n-octoxy benzophenone. Examples of plasticizers include dioctyl-4,5-epoxy-hexahydrophthalate, tris-(octoxycarbonylethyl)isocyanurate, tristearin and epoxidized soybean oil. Examples of the antistatic agent include glycerol monostearate, sodium stearyl sulfonate, and sodium dodecylbenzenesulfonate. Examples of mold releasing agents include stearyl stearate, beeswax, montan wax and paraffin wax. Examples of other resins include but are not limited to polypropylene, polystyrene, polymethyl methacrylate, and polyphenylene oxide. Combinations of any of the foregoing additives may be used. Such additives may be mixed at a suitable time during the mixing of the components for forming the composition.

In addition to the polymer and coloring material, the composition may optionally include various additives ordinarily incorporated in resin compositions of this type. Such additives may include UV absorbers; stabilizers, such as light and thermal stabilizers (e.g., acidic phosphorous-based compounds); hindered phenols; zinc oxide, zinc sulfide particles, or combination thereof; lubricants (mineral oil, and the like); plasticizers; antioxidants; anti-static agents (tetra alkylammonium benzene sulfonate salts, tetra alkylphosphonium benzene sulfonate salts, and the like); mold releasing agents (pentaerythritol tetrastearate; glycerol monstearate, and the like); and the like, and combinations comprising at least one of the foregoing additives. For example, the substrate can comprise about 0.01 weight percent wt % to about 0.5 wt % heat stabilizer; about 0.01 wt % to about 0.2 wt % antistatic agent; and about 0.1 wt % to about 1 wt % mold releasing agent; based upon the total weight of the polymer.

Some possible antioxidants include, for example, organophosphites, e.g., tris(nonyl-phenyl)phosphite, tris(2,4-di-t-butylphenyl)phosphite, bis(2,4-di-t-butylphenyl)pentaerythritol diphosphite, distearyl pentaerythritol diphosphite and the like; alkylated monophenols, polyphenols and alkylated reaction products of polyphenols with dienes, such as, for example, tetrakis[methylene(3,5-di-tert-butyl-4-hydroxyhydrocinnamate)]methane, 3,5-di-tert-butyl-4-hydroxyhydrocinnamate octadecyl, 2,4-di-tert-butylphenyl phosphite, and the like; butylated reaction products of para-cresol and dicyclopentadiene; alkylated hydroqulinones; hydroxylated thiodiphenyl ethers; alkylidene-bisphenols; benzyl compounds; esters of beta-(3,5-di-tert-butyl-4-hydroxyphenyl)-propionic acid with monohydric or polyhydric alcohols; esters of beta-(5-tert-butyl-4-hydroxy-3-methylphenyl)-propionic acid with monohydric or polyhydric alcohols; esters of thioalkyl or thioaryl compounds, such as, for example, distearylthiopropionate, dilaurylthiopropionate, ditridecylthiodipropionate, and the like; amides of beta-(3,5-di-tert-butyl-4-hydroxyphenyl)-propionic acid; and the like, as well as combinations comprising at least one of the foregoing antioxidants.

The block copolyestercarbonates may also be employed as additives for other polymers, especially polycarbonates, polyesters and addition polymers. The polycarbonates in the blend compositions of the invention are, for the most part, similar in molecular structure to the carbonate blocks of the block copolyestercarbonate as described hereinabove, with bisphenol A homo- and copolycarbonates generally being preferred. The polyesters are most often poly(alkylene dicarboxylates) and especially poly(alkylene arenedioates), with poly(ethylene terephthalate) and poly(1,4-butylene terephthalate) being preferred. Addition polymers include homopolymers and copolymers, especially copolymers of alkenylaromatic compounds, such as styrene, with ethylenically unsaturated nitriles, such as acrylonitrile and methacrylonitrile; dienes, such as butadiene and isoprene; and acrylic monomers, such as ethyl acrylate. These include the ABS (acrylonitrile-butadiene-styrene) and ASA (acrylonitrile-styrene-alkyl acrylate) graft copolymers.

The blend compositions of the invention may be prepared by such conventional operations as solvent blending and melt blending as by extrusion. They may additionally contain art-recognized additives including pigments, dyes, impact modifiers, stabilizers, flow aids and mold release agents. It is intended that the blend compositions include simple physical blends and any reaction products thereof, as illustrated by polyester-polycarbonate transesterification products.

Proportions of the block copolyestercarbonates in such blends are determined chiefly by the resulting proportions of arylate blocks, which are the active ionizing radiation stable improving entities, typical proportions providing about 3–85% by weight of arylate blocks in the blend. Routine experimentation may be used to determine acceptable maxima by testing yellowing performance upon irradiation as described herein. By reason of some degree of incompatibility between the block copolyarylestercarbonates of the invention and the polycarbonates and polyesters in which they may be incorporated, said blends are often not transparent. However, transparent blends, which are necessary for use in most medical articles and devices may be prepared by adjusting the length of the arylate blocks in the block copolyarylestercarbonates. A block length of around 10–20 repeating units is preferred for producing transparent blends. One preferred method to control the block length of the polyarylester block is to regulate the amount of resorcinol present in the reaction mixture with the aromatic diacid chloride or combination of aromatic diacid chlorides. An increase in the amount of resorcinol will reduce the block length of the resultant polyarylester block. For example, to achieve a weight average block length of about 10,000 to 15,000 molecular weight units (as measured by GPC using polycarbonate standards) a 10 times molar excess of resorcinol relative to moles of the diacid chloride in the reaction mixture is preferred, whereas to achieve a weight average block length of about 5500 molecular weight units (as measured by GPC using polycarbonate standards) a 30 times molar excess of resorcinol relative to the moles of the diacid chlordie is prefered. The other properties of said blends are excellent and comparable to those of bisphenol-A polycarbonate.

One particular example of a polyaryl-ester according to the present invention is according to Formula IX shown in FIG. 9.

EXAMPLES

Figure 3:
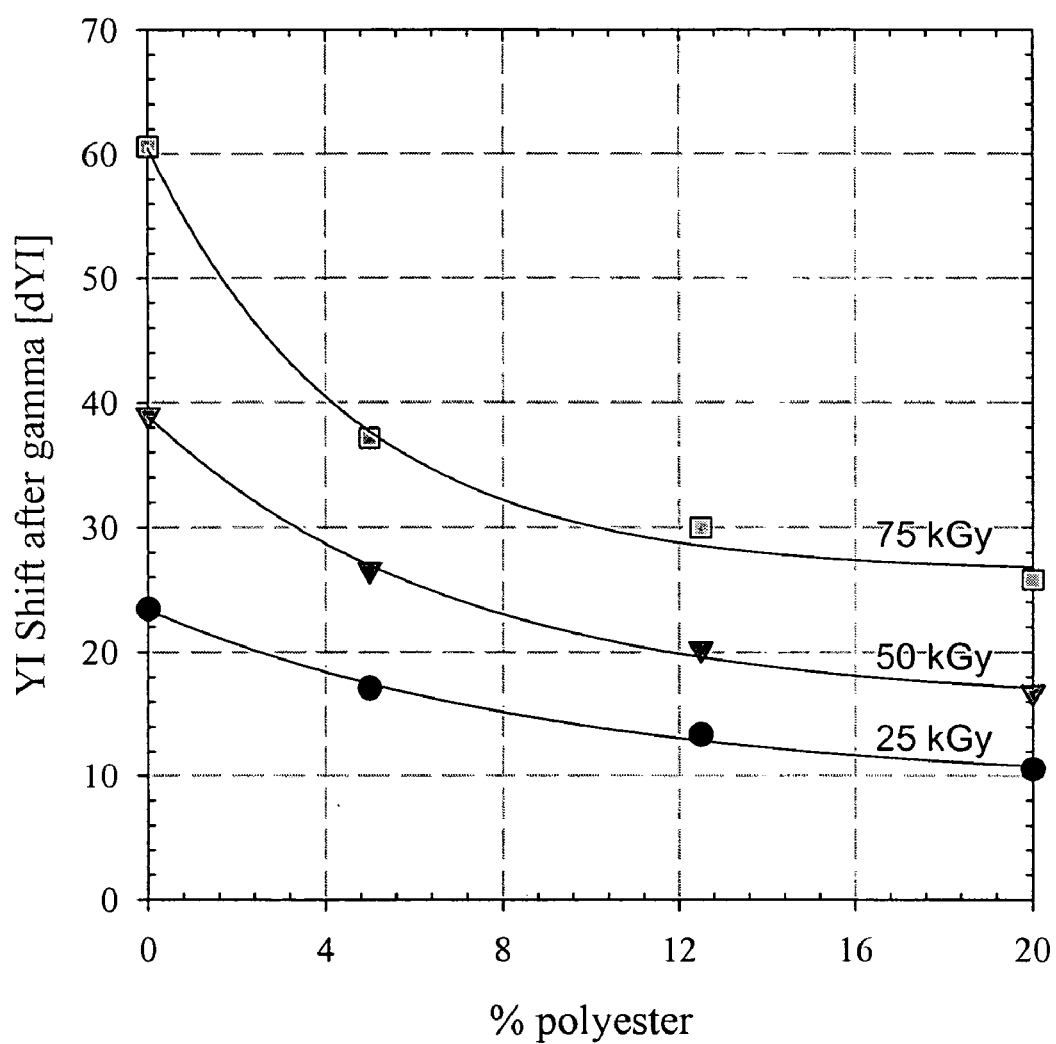
FIG. 3 is a table showing graphical representation of the changes in the initial yellowness (dYI) for bisphenol-A polycarbonate compositions for blends of polyarylestercarbonate resin with various bisphenol-A polycarbonate at 3 different ionizing radiation radiation dosage levels. There is no ionizing radiation stabilizing additive present.

Data illustrating improvements in ionizing radiation sterilization stabilization for copolyarylestercarbonates having resorcinol arylate units of the present invention versus bisphenol-A polycarbonate is provided in FIGS. 3 and 6. The test samples used to generate the data in FIG. 6 were molded parts produced by extrusion of the resin compositions made according to the above descriptions having the formula shown in FIG. 9 that were molded into plaques which in turn were subjected to ionizing radiation irradiation. The change in yellowness (dYI) was measured before and after the plaques were subjected to the ionizing radiation sterilization process. The copolyesterarylates used to generate this data possessed ester contents of about 20% and were formed from the reaction of resorcinol with a 1:1 ratio of terephthalic acid chloride and isophthalic acid chloride. After the block was formed, bisphenol-A and phosgene and a p-cumylphenol end-capping agent were added to complete the formation of the block copolyarylestercarbonate. The arylate block weight-averaged molecular weight was estimated to be about 5500 molecular weight units (using polycarbonate gel permeation chromatography standards). In FIG. 6, 20% polyester means that the sample contained 100% of the polyarylestercarbonate described above (which has an ester content of about 20%), while 0% polyester means that this sample contained only polycarbonate and that no polyarylestercarbonate was present. Intermediate percentages correspond to blends of polycarbonate with the polyestercarbonate having 20 weight percent polyester content. Specifically, the two samples labeled 5% and 13% in polyester in FIG. 6 were samples obtained from blending of the polyarylestercarbonate described above with polycarbonate. The blends were transparent, and had mechanical properties typically associated with polycarbonate resins. The yellowness shift results (dYI) in FIGS. 3 and 6 clearly show that the copolyarylestercarbonates of the present invention improve the ionizing radiation resistance performance by greater than 100% versus the polycarbonate control sample at the three commonly used ionizing radiation irradiation dosage levels of 25 kGY, 50 kGY and 75 kGy.

The importance of having a resorcinol moiety present and in combination with an aryl acid moiety in the polyarylestercarbonate is illustrated by comparing a copolycarbonate containing 30% wt % resorcinol with the polyarylestercarbonate containing about the same wt % of resorcinol. The resorcinol co-polycarbonate showed a dYI of 27.4 at a dosage of 25 kGy of ionizing radiation, whereas the polyarylestercarbonate containing resorcinol units showed a dYI of only 5.9 at a dosage of 25 kGy of ionizing radiation. Polyarylestercarbonate compositions, which did not have resorcinol present, also showed worse yellowing than polyarylestecarbonates containing resorcinol.

Increasing the polyarylester content of the polyarylestercarbonate composition does, as expected, lead to further improvement in the ionizing radiation stable performance of the ionizing radiation stable compositions. These results are shown in FIG. 3 for polyarylester contents ranging from 0% to 20% polyester. Further increasing the polyarylester content to about 87% polyarylester resulted in still further improved dYI performance. For example, a polyarylestercarbonate having a polyarylester content of 87%, had dYIs of 5.9 (25 kGy), 7.8 (50 kGy) and 10.6 (75 kGY), while a polyarylestercarbonate composition that had 20 weight % polyarylester content had dYIs of 23.4 (25 kGy), 39 (50 kGy) and 60.6 (75 kGy).

To further investigate the importance of the ratio of isophthalic acid units and terephthalic units, the ratio of isophthalic and terephthalic were varied from about 2:1 to 1:1 in a polyarylestercarbonate composition which had about 82% polyester. No significant change in the dYI was observed (dYI of 6.0 for 2:1 ratio and dYI of 5.9 for 1:1 at 25 kGy).

Figure 4:
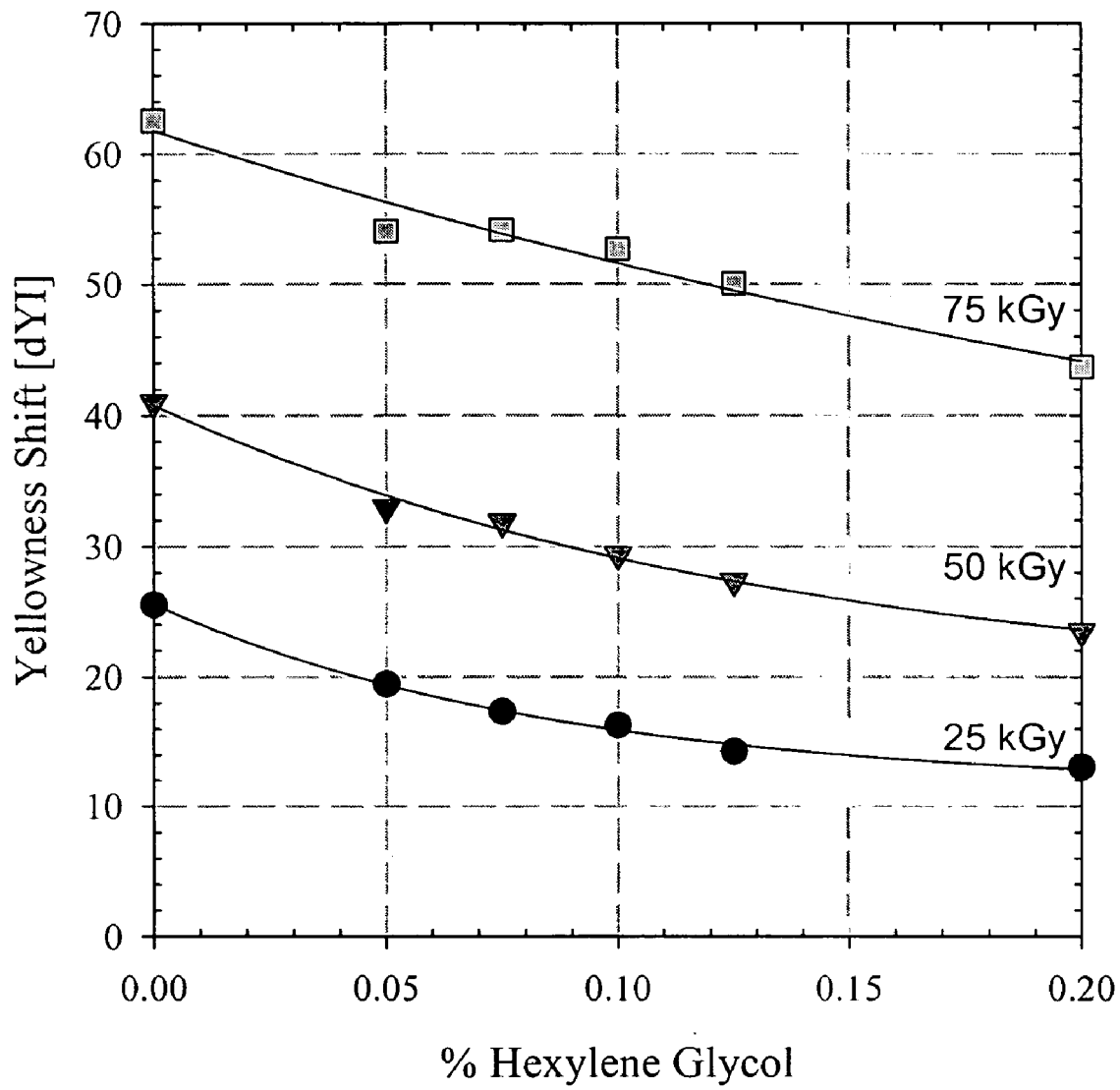
FIG. 4 is a table showing graphical representation of the changes in the initial yellowness (dYI) for bisphenol-A polycarbonate compositions having varying levels of percent (wt) hexylene glycol at 3 different ionizing radiation doses.
Figure 5:
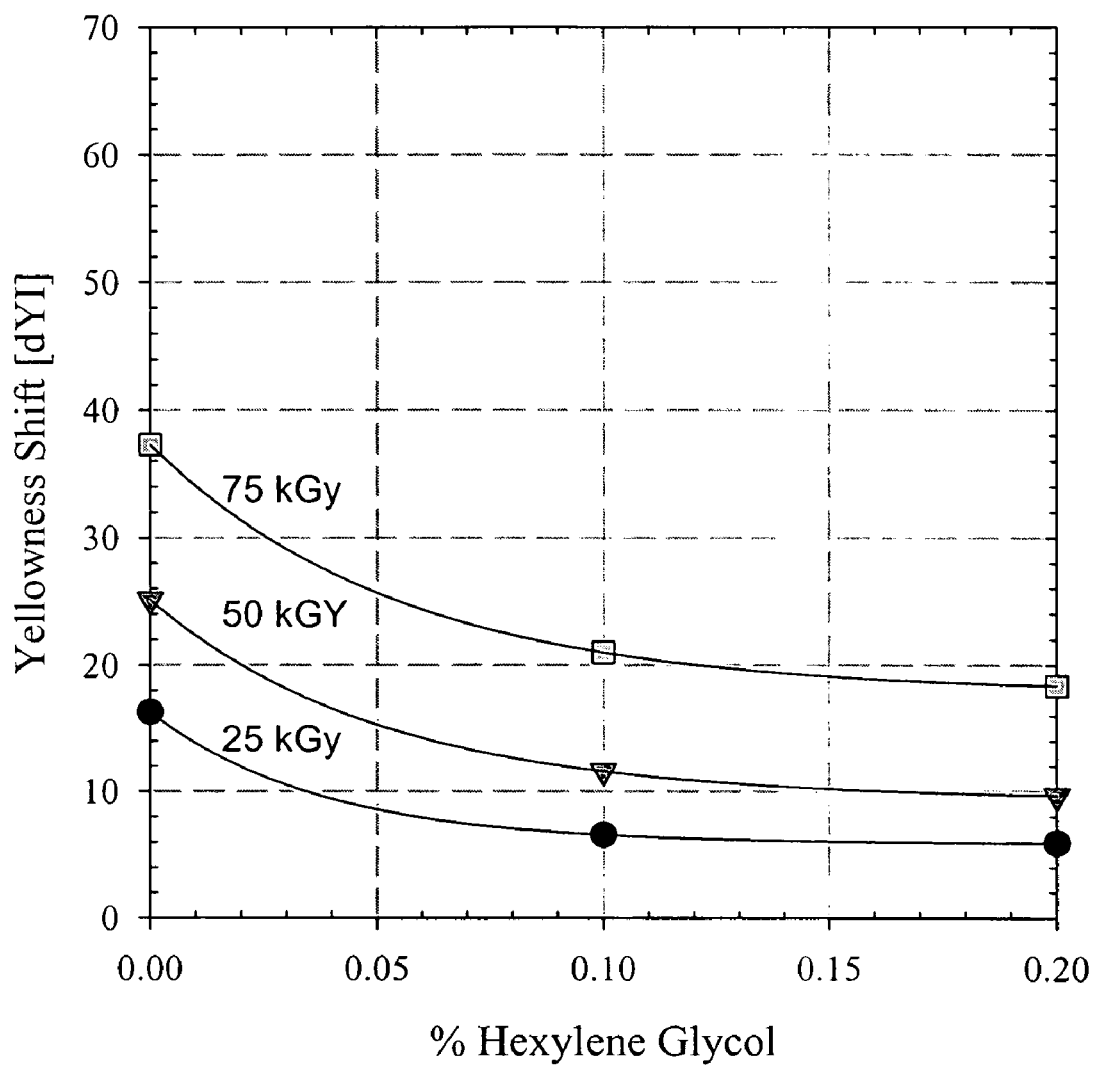
FIG. 5 is a graphical representation of the changes in the initial yellowness (dYI) for a 1:3 part blend of polyarylester-carbonate resin containing 20 wt % polyester content and bisphenol-A polycarbonate (total polyester content of 5%) having varying levels of percent (wt) hexylene glycol at 3 different ionizing radiation doses.

Surprisingly, synergistic improvements in ionizing radiation stability were obtained when the copolyarylestercarbonates of the present invention were combined with an ionizing radiation stabilizing additives. These improvements are shown in FIGS. 4, 5 and 7, which describe the yellowness change (dYI) for plaques made from a blend of the polyarylestercarbonate described above with bisphenol-A polycarbonate (in a 3:1 ratio) in combination with a ionizing radiation stabilization additive, hexylene glycol (also known as 2-methyl-2,4-pentanediol). At all three of the dosage levels a greater % dYI improvement was observed for the polyarylestercarbonate blends containing hexylene glycol versus a polycarbonate control. For example, the polyarylestercarbonate blend showed a 53% (25 kGY), 51% (50 kGy) and 38% (75 kGY) improvement in dYI when hexylene glycol was present (FIG. 5), whereas the polycarbonate control with hexylene glycol (FIG. 4) only showed a 36% (25 kGY), 28% (50 kGY) and 16% (75 kGy) improvement in dYI.

Other preferred possible ionizing radiation stable additives which could be used in the present invention include diols such as ethylene glycol, propylene glycol, 1,3-propanediol, 1,2-butanediol, 1,4butanediol, meso-2,3-butanediol, 1,2-pentanediol, 2,3-pentanediol, 1,4-pentanediol, 1,4-hexandiol and the like; alicyclic alcohols such as 1,2-cyclopentanediol, 1,2-cyclohexanediol, and the like; branched acyclic diols such as 2,3-dimethyl-2,3-butanediol (pinacol) and the like, polyols as well as alkoxy substituted cyclic or acyclic alkanes. Alkenols with sites of unsaturation are also a preferred class of alcohols. Examples include 4-methyl-4-penten-2-ol, 3-methyl-pentene-3-ol, 2-methyl-4-penten-2-ol, 2,4-dimethyl-4-pene-2-ol, and 9-decen-1-ol. Another preferred class of alcohols is the tertiary alcohols which contain at least one hydroxy substituted tertiary carbon. Specific of such tertiary alcohols-1-methyl-cyclohexane. Another useful class of alcohols is hydroxy methyl aromatics, which have hydroxy substitution on a saturated carbon attached to an unsaturated carbon in an aromatic ring. The hydroxy substituted saturated carbon may be a simple methylol group (—CH2OH) or it may be a member of a more complex hydrocarbon group such as would be the case with (—CR$^4$HOH) or (—CR$_2$$^4$OH) wherein R$^4$ is a complex or a simply hydrocarbon. Specific hydroxy methyl aromatics may be benzhydrol, 1,3-benzenedimethanol, benzylalcohol, 4-benzyl oxybenzyl alcohol and benzyl benzyl alcohol. Particularly preferred alcohols are 2-methyl-2,4-pentanediol (also known as hexylene glycol), polyethylene glycol, polypropylene glycol.

The photobleaching performance of the ionizing radiation stable compositions of the present invention was investigated and the results for 25 kGy and 75 kGy dosages of ionizing radiation are shown in FIG. 8. These measurements were made from plaques that were treated with ionizing radiation and then allowed to age in the dark for 14 days and then exposed to light without any further ionizing radiation treatment. Time 0 was recorded after the 14 days of dark aging. The yellowness of the plaques was measured on a regular schedule for the 28 days of light exposure as they photobleached. At both dosage levels the lowest YI values after 28 days of photobleaching were achieved from a composition formulated from the polyarylestercarbonate, bisphenol-A polycarbonate blend described above and hexylene glycol (0.1 wt % based on the total weight of the ionizing radiation stable formulation).

Preparation of Polyarylestercarbonate Resins: Methods for making polyarylestercarbonate resins are described in various patents including U.S. Pat. No. 6,559,270, which is incorporated by reference herein.

Blending Method: The polycarbonate resins used for blending with the polyarylestercarbonates of the present invention were either polycarbonate resins with a weight averaged molecular weight targets of 30,000 or 21,800 (as measured by gel permeation chromatography methods using polycarbonate standards or, where indicated) a combination of the two resins to achieve a melt flow index over a range of 7 to 26. The melt flow index was measured on extruded pellets using ISO procedure 1133 at 300° C. The ionizing radiation performance was found to be independent of the melt flow index for formulations with comparable polyarylester and/or hexylene glycol contents. Other additives, such as hexylene glycol, were mixed together with the polyarylestercarbonate and the polycarbonate prior to extrusion. The blends were then formed by extruding the mixtures on a single-screw or a twin-screw extruder using typical polycarbonate extrusion conditions (at about 550° F. melt temperature).

Ionizing radiation Irradiation Method: Samples were molded in 3"×4"×⅛" plaques and the YI were measured on a Gretag Color Eye 7000A instrument at settings of 2° angle and C illuminant in the transmission mode. The samples were then shipped to IBA Sterigenics in Westerville, Ohio for irradiation. Samples were irradiated at 25, 50, and 75 kGy and returned in sealed boxes. Of the irradiated chips, half were removed and the YI values measured on a Greytag Color Eye 7000A instrument. The remaining chips were stored, unexposed to light, for a period of two weeks. Y is were measured on the stored chips on a 7, 14, 21 and 28 day schedule to monitor the photobleaching over time. The results for various polyarylestercarbonate formulations and blends with and without the ionizing radiation additive, hexylene glycol are shown in FIG. 8.

The following claims should be read in view of the total specification's teachings and should not be read as limited to any particular embodiment of example described herein.

What is claimed is:

1. An irradiated article comprising: a block copolyarylestercarbonate and an ionizing radiation stabilizing additive, wherein said copolyarylestercarbonate comprises an organic carbonate block and at least one arylate block, said arylate block comprising arylate structural units derived from: (a) a 1,3-dihydroxybenzene, and (b) at least one aromatic dicarboxylic acid moiety, wherein the arylate block has a weight averaged molecular weight of between 2000 to about 20,000 and wherein the ionizing radiation stable additive is an aliphatic alcohol or a diaryl sulfide, and wherein the irradiated article has a yellowness shift of less than 40 yellowness index units after 75 kGY of ionizing radiation.

2. The irradiated article of claim 1, wherein the aromatic dicarboxylic acid moiety is selected from the group consisting of isophthalic acid, terephthalic acid, a halogen-substituted derivative of isophthalic acid, a halogen-substituted derivative of terephtlialic acid, and a mixture thereof.

3. The irradiated article of claim 2, wherein the ratio of arylate structural units derived from isophthalic acid or acid halide to terephthalic acid or acid halide is from 1:1 to 4:1.

4. The irradiated article of claim 1, wherein the organic carbonate blocks are derived from bisphenols selected from the group consisting of bisphenol-A, 1,3-dihydroxybenzene, and mixtures thereof.

5. The irradiated article of claim 1, wherein the at least one aromatic dicarboxylic acid moiety comprises a mixture of isophthalic acid or acid halide and terephthalic acid or acid halide in a molar ratio of about 1:1, and further wherein the organic carbonate block is derived from bisphenol-A.

6. The irradiated article of claim 1, wherein the arylester content in the copolyarylestercarbonate composition is between 10 wt % to 99wt % based on the weight of the copolyarylestercarbonate.

7. The irradiated article of claim 1, wherein, the composition further comprises one or more polycarbonate resins.

8. The irradiated article of claim 1, wherein the ionizing radiation stable additive is selected from a group consisting of polyethylene glycol, polypropylene glycol and hexylene glycol.

9. The irradiated article of claim 8, wherein the ionizing radiation stable additive is hexylene glycol.

10. The irradiated article of claim 9, wherein the hexylene glycol is present in the ionizing radiation stable composition in the range of 0.01 to 1 wt % based on the total weight of the ionizing radiation stable composition.

11. The irradiated article according to claim 1, wherein the composition has the formula I:

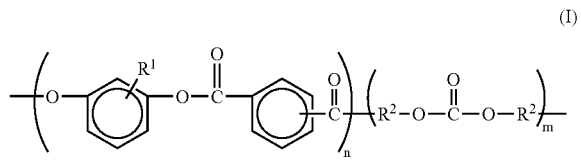

wherein m is an integer 1 or greater and n is an integer of 1 or greater wherein $R^1$ is hydrogen, halogen or $C_{1-4}$ alkyl, each $R^2$ is independently a divalent organic radical.

12. The irradiated article according to claim 11, wherein $R^1$ is hydrogen, $R^2$ is selected from the group consisting of resorcinol and bisphenol-A; and the copolyarylestercarbonate has end groups selected from the group consisting of hydroxyl groups, carboxylic acid groups, phenyl groups, and mixtures thereof.

13. An irradiated medical device comprising a composition that comprises a block copolyestercarbonate and an ionizing radiation stabilizing additive wherein the ionizing radiation stable additive is an aliphatic alcohol or a diaryl sulfide, wherein the copolyestercarbonate comprises an organic carbonate block and at least one arylate block, said arylate block comprising arylate structural units derived from: (a) at least one 1,3-dihydroxybenzene moiety, and (b) at least one aromatic dicarboxylic acid moiety, wherein the arylate block has a weight averaged molecular weight of between 2000 to about 20,000 and wherein the irradiated medical device has a yellowness shift of less than 40 yellowness index units after 75 kGY of ionizing radiation.

14. The medical device of claim 13, wherein the ionizing radiation stable additive is selected from a group consisting of polyethylene glycol, polypropylene glycol and hexylene glycol.

15. The medical device of claim 14, wherein the ionizing radiation stable additive is present in the ionizing radiation stable composition in the range of 0.01 to 1 wt % based on the total weight of the ionizing radiation stable composition.

16. An irradiated article comprising a composition that comprises a block copolyarylestercarbonate, wherein the copolyestercarbonate comprises an organic carbonate block and at least one arylate block, said arylate block comprising arylate structural units derived from (a) at least one 1,3-dihydroxybenzene moiety and at least one aromatic dicarboxylic acid moiety wherein the arylate block has a weight averaged molecular weight of between 2000 to about 20,000 and wherein the composition further comprises an ionizing radiation stabilizing additive, wherein the ionizing radiation stable additive comprises is an aliphatic alcohol or a diaryl sulfide and wherein the irradiated article has a yellowness shift of less than 30 yellowness index units after 75 kGY of ionizing radiation.

17. The article according to claim 16, wherein the article has a yellowness shift of less than 5 yellowness index units when a photobleaching steady state condition is reached after 25 kGy of ionizing radiation.

18. The article of claim 16, wherein the ionizing radiation stable additive is selected from a group consisting of polyethylene glycol, polypropylene glycol and hexylene glycol.

* * * * *